United States Patent [19]

Böttcher et al.

[11] Patent Number: 4,760,082
[45] Date of Patent: Jul. 26, 1988

[54] CERTAIN DI-ARYL-1,2,3,6-TETRAHYDRO-PYRIDYL-N-LOWER-ALKYLENE-PYRIDINES HAVING NEUROLEPTIC PROPERTIES

[75] Inventors: Henning Böttcher, Darmstadt; Andreas Fuchs, Hanover; Christoph Seyfried, Seeheim-Jugenheim, all of Fed. Rep. of Germany

[73] Assignee: Merck Patent Gesellschaft mit beschrankter Haftung, Darmstadt, Fed. Rep. of Germany

[21] Appl. No.: 15,188

[22] Filed: Feb. 13, 1987

Related U.S. Application Data

[62] Division of Ser. No. 789,223, Oct. 18, 1985, Pat. No. 4,665,187.

[30] Foreign Application Priority Data

Oct. 19, 1984 [DE] Fed. Rep. of Germany ....... 3438394

[51] Int. Cl.[4] ................... C07D 401/12; A61K 31/44
[52] U.S. Cl. ................................... 514/332; 514/333; 546/255; 546/266
[58] Field of Search ................ 546/255, 266; 514/332

[56] References Cited

U.S. PATENT DOCUMENTS 4,472,408  9/1984  Nisato et al. ................ 514/277
4,521,428  6/1985  Nisato et al. ................ 514/277

*Primary Examiner*—Alan L. Rotman
*Attorney, Agent, or Firm*—Millen & White

[57] ABSTRACT

New pyridine derivatives of the formula I

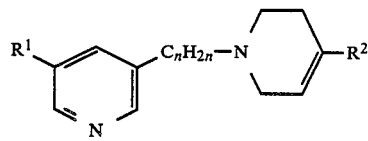

wherein $R^1$ and $R^2$ are each phenyl or 2- or 3-thienyl radicals which are unsubstituted or monosubstituted or di-substituted by alkyl, alkoxy, F, Cl, Br, OH and/or $CF_3$ and n is 1, 2 or 3, and the alkyl and alkoxy groups each have 1–4 C atoms, and salts thereof, have suppressant actions on the central nervous system, in particular neuroleptic actions.

18 Claims, No Drawings

CERTAIN DI-ARYL-1,2,3,6-TETRAHYDRO-PYRIDYL-N-LOWER-ALKYLENE-PYRIDINES HAVING NEUROLEPTIC PROPERTIES

This is a division, of application Ser. No. 789,223 filed Oct. 18, 1985, now U.S. Pat. No. 4,665,187.

SUMMARY OF THE INVENTION

It is an object of this invention to provide new compounds which can be used for the preparation of medicaments.

Upon further study of the specification and appended claims, further objects and advantages of this invention will become apparent to those skilled in the art.

These objects have been achieved by providing new pyridine derivatives of formula I

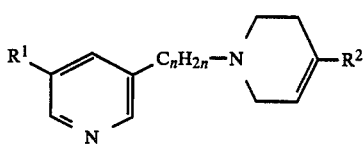

wherein $R^1$ and $R^2$ are independently each phenyl or 2- or 3-thienyl radicals which are unsubstituted or mono-substituted or disubstituted by alkyl, alkoxy, F, Cl, Br, OH and/or $CF_3$ and n is 1, 2 or 3, and the alkyl and alkoxy groups each have 1–4 C atoms, and salts thereof.

DETAILED DISCUSSION

It has been found that the compounds of this invention have useful pharmacological properties, coupled with good tolerance. Thus, for example, they exhibit actions which influence the central nervous system, preferably suppressing (for example sedating, tranquilizing, neuroleptic and/or antidepressant) actions. Specifically, the compounds have a suppressant action on the behavior of mice (for the method, compare Irwin, Psychopharmacologia 13 (1968), 222–257), inhibit apomorphine-induced climbing behavior in mice (for the method, compare Costall et al., European J. Pharmacol. 50 (1968), 39–50) or induce contralateral turning behavior in hemi-Parkinson rats (detectable by the method of Ungerstedt et al., Brain Res. 24 (1970), 485–493), without noticeable cataleptic side effects occurring (for the method, compare Dolini-Stola, Pharmakopsychiat. 6 (1973), 189–197). The substances furthermore inhibit bonding of tritiated dopamine agonists and antagonists to striated receptors (detectable by the method of Schwarcz et al., J. Neurochemistry 34 (1980), 772–778, and Creese et al., European J. Pharmacol., 46 (1977), 377–381). The compounds additionally inhibit the tongue/jaw reflex in anaesthetized rats (detectable in accordance with the methods of Barnett et al., European J. Pharmacol. 21 (1973), 178–182 and of Ilhan et al., European J. Pharmacol. 33 (1975), 61–64). Analgesic and hypotensive actions also arise; thus, the arterial blood pressure measured directly on conscious, spontaneously hypertensive rats carrying catheters (strain SHR/NIH-MO//CHB-EMD; for the method compare Weeks and Jones, Proc. Soc. Exptl. Biol. Med. 104 (1960), 646–648) is reduced following intragastral administration of the compounds.

Compounds of the formula I and their physiologically acceptable acid addition salts can therefore be used as, medicament active compounds and also as intermediate products for the preparation of other medicament active compounds.

The invention relates to the pyridine derivatives of the formula I and their salts.

In the radicals $R^1$ and $R^2$, alkyl is preferably methyl, and furthermore also ethyl, n-propyl, isopropyl, n-butyl, isobutyl, sec.-butyl or tert.-butyl. Alkoxy is preferably methoxy, and furthermore also ethoxy, n-propoxy, isopropoxy, n-butoxy, isobutoxy, sec.-butoxy or tert.-butoxy.

The radicals $R^1$ and $R^2$ are preferably unsubstituted phenyl. If $R^1$ and/or $R^2$ denote a substituted phenyl group, this is preferably monosubstituted.

However, it can also be disubstituted, it being possible for the substituents to be identical or different. Preferred substituents on the phenyl groups are methyl, ethyl, methoxy, ethoxy, F, Cl, Br and/or OH. Specifically, $R^1$ and $R^2$ are preferably phenyl, and furthermore o-, m- or p-tolyl, o-, m- or p-ethylphenyl, o-, m- or p-methoxyphenyl, o-, m- or p-ethoxyphenyl, o-, m- or p-fluorophenyl, o-, m- or p-chlorophenyl, o-, m- or p-bromophenyl, o-, m- or p-hydroxyphenyl, o-, m- or p-trifluoromethylphenyl, 2,3-, 2,4-, 2, -, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dihydroxyphenyl, 2-methyl-4-chlorophenyl, 2- or 3-thienyl or 5-methyl-2-thienyl.

The parameter n is preferably 1, and the radical $-C_nH_{2n}-$ is preferably $-CH_2-$, or furthermore preferably $-CH(CH_3)-$, $-(CH_2)_2-$ or $-(CH_2)_3-$.

The invention accordingly particularly relates to those compounds of the formula I in which at least one of the radicals mentioned has one of the abovementioned meanings, in particular the abovementioned preferred meanings. Some preferred groups of compounds can be expressed by the following part formulae Ia to Ij, which correspond to the formula I and in which the radicals and parameters not described in more detail have the meaning given in the case of formula I, but wherein in Ia $R^1$ is phenyl, tolyl, methoxyphenyl, fluorophenyl, chlorophenyl, hydroxyphenyl, trifluoromethylphenyl, dimethoxyphenyl or thienyl;

in Ib $R^1$ is phenyl, o-, m- or p-tolyl, m- or p-methoxyphenyl, p-fluorophenyl, p-chlorophenyl, m-or p-hydroxyphenyl, m-trifluoromethylphenyl, 3,4-dimethoxyphenyl or 2-thienyl;

in Ic $R^1$ is phenyl;

in Id $R^2$ is phenyl, tolyl, methoxyphenyl, fluorophenyl, chlorophenyl, trifluoromethylphenyl, chloro-trifluoromethylphenyl or thienyl;

in Ie $R^2$ is phenyl, o-, m- or p-tolyl, p-methoxyphenyl, p-fluorophenyl, p-chlorophenyl, m-trifluoromethylphenyl or 2- or 3-thienyl;

in If $R^2$ is phenyl;

in Ig $C_nH_{2n}$ is $-CH_2-$, $-CH(CH_3)-$, $-(CH_2)_2-$ or $(CH_2)_3-$;

in Ih $C_nH_{2n}$ is $-CH_2-$;

in Ii $R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl or 2-thienyl, $R^2$ is phenyl, o-, m- or p-tolyl, p-methoxyphenyl, p-fluorophenyl, p-chlorophenyl, m-trifluoromethylphenyl or 2- or 3-thienyl and
$C_nH_{2n}$ is $-CH_2-$, $-CH(CH_3)-$, $-(CH_2)_2-$ or $-(CH_2)_3-$; and in Ij $R^1$ is phenyl, m- or p-methoxyphenyl, p-fluorophenyl, m-hydroxyphenyl or 3,4-dimethoxyphenyl,
$R^2$ is phenyl and
$C_nH_{2n}$ is $-CH_2-$.

Some compounds of the formula I can have one or more asymmetric carbon atoms. They can therefore exist as racemates, as mixtures of several racemates, if several asymmetric carbon atoms are present, and in various optically active forms.

The invention furthermore relates to a process for the preparation of the compounds of the formula I and of their salts characterized in that a compound of the formula II $$Py\text{-}A\text{-}X^1 \qquad \text{II}$$

wherein Py is the 5-$R^1$-3-pyridyl radical, A is the group $-C_nH_{2n}-$, $X^1$ is $NH_2$ or X, and X is Cl, Br, I, OH or a reactively functionally modified OH group, is reacted with a compound of the formula III $$X^2\text{---}CH_2CH_2\text{---}CR^2\text{=}CH\text{---}CH_2\text{---}X^3 \qquad \text{III}$$

wherein $X^2$ and $X^3$ are identical or different and, if $X^1$ is $NH_2$, are each X, or otherwise together are NH, and $R^2$ has the meaning given, or in that a compound which otherwise corresponds to the formula I but contains one or more reducible groups and/or one or more additional C—C and/or C—N bonds instead of one or more hydrogen atoms, is treated with a reducing agent, or in that a compound of the formula IV

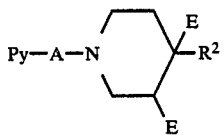

wherein one radical E is X, CN or $NH_2$ and the other radical E is H and Py, A, R and X have the meanings given, is treated with an agent which splits off HE, and/or in that, if appropriate, an O-alkyl group in a compound of the formula I is split to form an OH group, and/or in that a base of the formula I is converted into one of its salts by treatment with an acid.

The compounds of the formula I are otherwise prepared by methods which are known per se, such as are described in the literature (for example in the standard works, such as Houben-Weyl, Methoden der Organischen Chemie (Methods of Organic Chemistry), Georg-Thieme-Verlag, Stuttgart; Organic Reactions, John Wiley & Sons, Inc., N.Y.), and in particular under reaction conditions such as are known and suitable for the reactions mentioned. Variants which are known per se and are not mentioned here in more detail can also be utilized.

If desired, the starting substances for the process claimed can also be formed in situ, in a manner such that they are not isolated from the reaction mixture but are immediately reacted further to give the compounds of the formula I.

In the compounds of the formula II, $X^1$ is preferably X; accordingly, in the compounds of the formula III, $X^2$ and $X^3$ are preferably together NH. The radical X is preferably Cl or Br; however, it can also be I, OH or a reactively functionally modified OH group, in particular alkylsulfonyloxy with 1–6 (for example methanesulfonyloxy) or arylsulfonyloxy with 6–10 C atoms (for example benzenesulfonyloxy, p-toluenesulfonyloxy or 1- or 2-naphthalene-sulfonyloxy).

The compounds of the formula I are accordingly obtainable, in particular, by reaction of compounds of the formula Py-A-Cl or Py-A-Br with tetrahydropyridine derivatives of the formula III wherein $X^2$ and $X^3$ together are an NH group (called IIIa below).

The compounds of the formulae II and, in particular, III are known in some cases; the compounds of the formulae II and III which are not known can easily be prepared analogously to the known compounds. Primary alcohols of the formula Py-A-OH are obtainable, for example, by reduction of the corresponding carboxylic acids or their esters. Treatment with thionyl chloride, hydrogen bromide, phosphorus tribromide or similar halogen compounds gives the corresponding halides of the formula Py-A-Hal. The corresponding sulfonyloxy compounds are obtainable from the alcohols Py-A-OH by reaction with the corresponding sulfonic acid chlorides. The iodine compounds of the formula Py-A-I are obtainable, for example, by the action of potassium iodide on the associated p-toluenesulfonic acid esters. The amines of the formula Py-A-$NH_2$ can be prepared, for example, from the halides with potassium phthalimide or by reduction of the corresponding nitriles.

The tetrahydropyridine derivatives IIIa are known in most cases (compare German Offenlegungsschrift 2,060,816) and are obtainable, for example, by reaction of 4-piperidone with organometallic compounds of the formula M-$R^2$ (wherein M is an Li atom or MgHal), subsequent hydrolysis to give the corresponding 4-$R^2$-4-hydroxypiperidines and subsequent dehydration to give 4-$R^2$-3,4-dehydro-piperidines. Compounds of the formula III ($X^2$ and $X^3$ are each X) can be prepared, for example, by reduction of diesters of the formula AlkylOOC—$CH_2$—$CR^2$=CH—COOAlkyl to diols of the formula HO—$CH_2CH_2$—$CR^2$=CH—$CH_2$OH (III, $X^1$=$X^2$=OH) and, if appropriate, subsequent reaction with $SOCl_2$ or $PBr_3$.

The reaction of the compounds II and III proceeds by methods such as are known from the literature for alkylation of amines. The components can be melted with one another, if appropriate in a closed tube or in an autoclave, in the absence of a solvent. However, it is also possible to react the compounds in the presence of an inert solvent. Examples of suitable solvents are hydrocarbons, such as benzene, toluene or xylene; ketones, such as acetone or butanone; alcohols, such as methanol, ethanol, isopropanol or n-butanol; ethers, such as tetrahydrofuran (THF) or dioxane; amides, such as dimethylformamide (DMF) or N-methyl-pyrrolidone; nitriles, such as acetonitrile, and if appropriate also mixtures of these solvents with one another or mixtures with water. The addition of an acid-binding agent, for example an alkali metal hydroxide, carbonate or bicarbonate or an alkaline earth metal hydroxide, carbonate or bicarbonate, or another alkali metal or alkaline earth metal salt of a weak acid, preferably a potassium, sodium or calcium salt, or the addition of an organic base, such as triethylamine, dimethylaniline, pyridine or quinoline, or of an excess of the amine component Ind-A-NH$_2$ or of the piperidine derivative of the formula IIIa, may be advantageous. The reaction time is between a few minutes and 14 days and the reaction temperature is between about 0° and 150°, usually between 20° and 130°, depending on the conditions applied.

It is furthermore possible to obtain a compound of the formula I by treating a precursor which contains one or more reducible group(s) and/or one or more additional C—C and/or C—N bond(s), instead of hydrogen atoms, with a reducing agent, preferably at temperatures between −80° and +250°, in the presence of at least one inert solvent.

Reducible groups (replaceable by hydrogen) are, in particular, oxygen in a carbonyl group, hydroxyl, arylsulfonyloxy (for example p-toluenesulfonyloxy), N-benzenesulfonyl, N-benzyl or O-benzyl.

It is in principle possible to convert compounds which contain only one of these groups or additional bonds or those which contain two or more of these groups or additional bonds side by side into a compound of the formula I by reduction. This is preferably carried out using nascent hydrogen or complex metal hydrides, and furthermore by the Wolff-Kishner reduction.

Preferred starting substances for the reduction correspond to the formula V

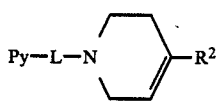

V wherein L is a chain corresponding to the radical A but wherein one or more —CH$_2$—group(s) are replaced by —CO— and/or one or more hydrogen atoms are replaced by OH groups.

In the compounds of the formula V, L is preferably —(CH$_2$)$_{n-1}$—CO—[specifically —CO—, —CH$_2$—CO— or —CH$_2$CH$_2$—CO—], and furthermore, for example, —CH(CH$_3$)—CO—, —COCH$_2$—, —CO-CO—, —COCH$_2$CO—, —CO—CH$_2$CH$_2$—, —CH$_2$CO—CH$_2$—, —CHOH—, —CH$_2$—CHOH—, —(CH$_2$)$_2$—CHOH—, —CHOH—CH$_2$— or —CHOH—CO—.

Compounds of the formula V can be prepared, for example, by reacting IIIa with a compound of the formula VI

 Py-L-X$^1$  VI wherein Py, L and X$^1$ have the abovementioned meanings, under the conditions which are described above for the reaction of II and III.

If nascent hydrogen is used as the reducing agent, this can be produced, for example, by treatment of metals with weak acids or with bases. Thus, for example, a mixture of zinc with an alkali metal hydroxide solution or of iron with acetic acid can be used. The use of sodium or another alkali metal in an alcohol, such as ethanol, isopropanol, butanol or amyl or isoamyl alcohol or phenol is also suitable. An aluminum/ nickel alloy in alkaline-aqueous solution, if appropriate with the addition of ethanol, can furthermore be used. Sodium amalgam or aluminum amalgam in aqueous-alcoholic or aqueous solution are also suitable for producing nascent hydrogen. The reaction can also be carried out in a heterogeneous phase system, an aqueous phase and a benzene or toluene phase advantageously being used.

Complex metal hydrides, such as LiAlH$_4$, NaBH$_4$, diisobutylaluminum hydride or NaAl(OCH$_2$CH$_2$OCH$_3$)$_2$H$_2$, and diborane can furthermore be particularly advantageously used as the reducing agent, if desired with the addition of catalysts, such as BF$_3$, AlCl$_3$ or LiBr. Solvents which are particularly suitable for this purpose are ethers, such as diethyl ether, di-n-butyl ether, THF, dioxane, diglyme or 1,2-dimethoxyethane, and hydrocarbons, such as benzene. Solvents which are suitable for reduction with NaBH$_4$ are, above all, alcohols, such as methanol or ethanol, and furthermore water and aqueous alcohols. The reduction by these methods is preferably carried out at temperatures between −80° and +150°, in particular between about 0° and about 100°.

—CO—groups in acid amides (for example those of the formula V wherein L is —(CH$_2$)$_{n-1}$—CO—) can be particularly advantageously reduced to CH$_2$ groups with LiAlH$_4$ in THF at temperatures between about 0° and 66°.

It is furthermore possible to reduce one or more carbonyl groups to CH$_2$ groups by the Wolff-Kishner method, for example by treatment with anhydrous hydrazine in absolute ethanol under pressure at temperatures between about 150° and 250°. A sodium alcoholate is advantageously used as the catalyst. The reduction can also be varied according to the method of Huang-Minlon, by carrying out the reaction with hydrazine hydrate in a high-boiling, water-miscible solvent, such as diethylene glycol or triethylene glycol, in the presence of an alkali, such as sodium hydroxide. The reaction mixture is as a rule boiled for about 3–4 hours. The water is then distilled off and the hydrazone formed is decomposed at temperatures up to about 200°. The Wolff-Kishner reduction can also be carried out at room temperature in dimethyl sulphoxide with hydrazine.

Compounds of the formula I are furthermore obtained by splitting off HE from compounds of the formula IV to form a double bond. In accordance with the definition of E, this can be, for example, splitting off of hydrogen halide, water (dehydration), a carboxylic acid or another acid, ammonia or HCN. The starting substances of the formula IV are obtainable, for example, by reacting II (X$^1$=X) with a compound of the formula VII

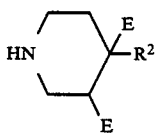

VII wherein E and R$^2$ have the meanings given.

If one of the radicals E is Hal, this substituent can easily be eliminated under basic reaction conditions. Bases which can be used are: alkali metal hydroxides, alkali metal carbonates, alcoholates, such as, for example, potassium tert.-butylate, and amines, such as, for example, dimethylaniline, pyridine, collidine or quinoline; examples of solvents which are used are benzene, toluene, cyclohexane, THF and tert.-butanol. The amines used as bases can also be employed in excess as the solvent. If one of the radicals E is an OH group, acids, such at acetic acid, hydrochloric acid or mixtures of the two, are preferably used as the dehydrating agent. It may be advantageous to add a solvent (for example water of ethanol). Elimination of acyl, alkylsulfonyl and alkoxysulfonyloxy or amino radicals can be carried out under similar conditions. Elimination of sulfonic acid radicals, for example those of the mesylates or tosylates, is carried out under gentle conditions by boiling with alkali metal carbonates, for example $Li_2CO_3$, or with potassium acetate in DMF or dimethyl sulphoxide. Ammonia can already be split off by heating the salts of the corresponding amino compounds (in particular the 4-amino derivatives). HCN can be split off from compounds of the formula IV (one group E=CN) in a similar manner by heating. The elimination of HE from IV is generally carried out at temperatures between 0° and about 250°preferably between 50° and 200°.

If appropriate, a compound of the formula I can furthermore be converted into another compound of the formula I by methods which are known per se.

Thus, ethers (O-alkyl derivatives) can be split, the corresponding hydroxy derivatives being formed. For example, the ethers can be split by treatment with a dimethyl sulphide-boron tribromide complex, for example in toluene, 1,2-dichloroethane, THF or dimethyl sulphoxide, or by melting with pyridine hydrohalides or aniline hydrohalides, preferably pyridine hydrochloride, at about 150°–250°.

The resulting base of the formula I can be converted into the associated acid addition salt with an acid. Acids which are preferably suitable for this reaction are those which give physiologically acceptable salts. Thus, it is possible to use inorganic acids, for example sulfuric acid, hydrogen halide acids, such as hydrochloric acid or hydrobromic acid, phosphoric acids, such as orthophosphoric acid, nitric acid and sulfamic acid, and furthermore organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-mono- and -disulfonic acids and lauryl-sulfuric acid. Acid addition salts which are not physiologically acceptable (for example picrates) may be suitable for isolation and purification of bases of the formula I.

If desired, the free bases of the formula I can be liberated from their salts by treatment with strong bases, such as sodium hydroxide or potassium hydroxide or sodium carbonate or potassium carbonate.

The invention furthermore relates to the use of the compounds of the formula I and their physiologically acceptable salts for the preparation of pharmaceutical formulations, in particular by a non-chemical route. For this, they can be brought into a suitable dosage form together with at least one excipient or auxiliary and, if appropriate, in combination with one or more other active compound(s).

The invention furthermore relates to agents, in particular pharmaceutical formulations, containing at least one compound of the formula I and/or one of its physiologically acceptable salts. These formulations can be employed as medicaments in human medicine or veterinary medicine. Possible excipients are organic or inorganic substances which are suitable for enteral (for example oral) or parenteral administration or topical application and with which the new compounds do not react, for example water, vegetable oils, benzyl alcohols, polyethylene glycols, gelatine, carbohydrates, such as lactose or starch, magnesium stearate, talc or vaseline. Formulations which are used for enteral administration are, in particular, tablets, coated tablets, capsules, syrups, elixirs, drops or suppositories, those which are used for parenteral administration are solutions, preferably oily or aqueous solutions, and furthermore suspensions, emulsions or implants, and those which are used for topical application are ointments, creams or powders. The new compounds can also be lyophilized and the lyophilizates obtained can be used, for example, for the preparation of injection products.

The formulations mentioned can be sterilized and/or contain auxiliaries, such as lubricants, preservatives, stabilizers and/or wetting agents, emulsifiers, salts for influencing the osmotic pressure, buffer substances, colorants, flavor substances and/or aroma substances. If desired, they can also contain one or more other active compounds, for example one or more vitamins.

The invention furthermore relates to the use of the compounds of the formula I and their physiologically acceptable salts in the therapeutic treatment of the human or animal body and in combating diseases, in particular schizophrenia, psychoreactive disorders and psychopathies, depressions, severe chronic pain and diseases accompanied by increased blood pressure.

The compounds can furthermore be used in the treatment of extrapyramidal disorders.

The substances according to the invention are thereby as a rule administered analogously to known commercially available products (thioridazine and dihydroergocristine), preferably in dosages between about 0.2 and 500 mg, in particular between 0.2 and 50 mg, more particularly between 2 and 50 mg per dosage unit. The daily dosage is preferably between about 0.003, and 10 mg/kg of body weight, more preferably 0.003 to 1 mg/kg, most preferably 0.03 to 1 mg/kg.

However, the specific dose for each particular patient depends on the most diverse factors, for example on the efficacy of the specific compound employed, and on the age, body weight, general state of health, sex, diet, time and route of administration, rate of elimination and medicament combination and the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight; unless otherwise indicated.

In the following examples, "customary working up" means: water is added, if necessary, the mixture is extracted with methylene chloride, the organic phase is separated off, dried over sodium sulfate and filtered, the filtrate is evaporated and the residue is purified by chromatography on silica gel and/or by crystallization. Temperatures are given in °C. Rf values have been determined by thin layer chromatography on silica gel.

EXAMPLE 1

A solution of 26.3 g of 3-methylsulfonyloxy-methyl-5-phenyl-pyridine (obtainable by reduction of 5-phenyl-pyridine-3-carboxylic acid with LiAlH$_4$ to give 3-hydroxy-methyl-5-phenyl-pyridine and mesylation) and 16 g of 4-phenyl-1,2,3,6-tetrahydropyridine in 100 ml of acetonitrile is stirred at 20° for 12 hours and worked up in the customary manner to give 3-(4-phenyl-1,2,3,6-tetrahydropyridyl-methyl)-5-phenyl-pyridine ("P"), melting point: 80°–82°. Dihydrochloride, melting point: 218°–220°.

The following compounds are obtained analogously from the corresponding methanesulfonates, chlorides or bromides:

3-(4-phenyl-1,2,3,6-tetrahydropyridyl-methyl)-5-o-tolyl-pyridine
3-(4-phenyl-1,2,3,6-tetrahydropyridyl-methyl)-5-m-tolyl-pyridine
3-(4-phenyl-1,2,3,6-tetrahydropyridyl-methyl)-5-p-tolyl-pyridine
3-(4-phenyl-1,2,3,6-tetrahydropyridyl-methyl)-5-m-methoxy-phenyl-pyridine, melting point: 133°–135°
3-(4-phenyl-1,2,3,6-tetrahydropyridyl-methyl)-5-p-methoxy-phenyl-pyridine, dihydrochloride, melting point: 239°–240°
3-(4-phenyl-1,2,3,6-tetrahydropyridyl-methyl)-5-p-fluoro-phenyl-pyridine, melting point 128°–129°
3-(4-phenyl-1,2,3,6-tetrahydropyridyl-methyl)-5-p-chloro-phenyl-pyridine
3-(4-phenyl-1,2,3,6-tetrahydropyridyl-methyl)-5-m-hydroxy-phenyl-pyridine, dihydrochloride, melting point: 206°–208°
3-(4-phenyl-1,2,3,6-tetrahydropyridyl-methyl)-5-p-hydroxy-phenyl-pyridine
3-(4-phenyl-1,2,3,6-tetrahydropyridyl-methyl)-5-m-trifluoro-methylphenyl-pyridine
3-(4-phenyl-1,2,3,6-tetrahydropyridyl-methyl)-5-(3,4-dimethoxyphenyl)-pyridine dihydrochloride melting point: 216°–218°
3-(4-phenyl-1,2,3,6-tetrahydropyridyl-methyl)-5-(2-thienyl)-pyridine
3-(4-o-tolyl-1,2,3,6-tetrahydropyridyl-methyl)-5-phenyl-pyridine
3-(4-m-tolyl-1,2,3,6-tetrahydropyridyl-methyl)-5-phenyl-pyridine
3-(4-p-tolyl-1,2,3,6-tetrahydropyridyl-methyl)-5-phenyl-pyridine
3-(4-p-methoxyphenyl-1,2,3,6-tetrahydropyridyl-methyl)-5-phenyl-pyridine
3-(4-p-fluorophenyl-1,2,3,6-tetrahydropyridyl-methyl)-5-phenyl-pyridine
3-(4-p-chlorophenyl-1,2,3,6-tetrahydropyridyl-methyl)-5-phenyl-pyridine
3-(4-m-trifluoromethylphenyl-1,2,3,6-tetrahydropyridyl-methyl)-5-phenyl-pyridine
3-[4-(4-chloro-3-trifluoromethylphenyl)-1,2,3,6-tetrahydro-pyridyl-methyl]-5-phenyl-pyridine
3-[4-(2-thienyl)-1,2,3,6-tetrahydropyridyl-methyl]-5-phenyl-pyridine
3-[4-(2-thienyl)-1,2,3,6-tetrahydropyridyl-methyl]-5-m-tolyl-pyridine
3-[4-(2-thienyl)-1,2,3,6-tetrahydropyridyl-methyl]-5-p-tolyl-pyridine
3-[4-(2-thienyl)-1,2,3,6-tetrahydropyridyl-methyl]-5-p-fluorophenyl-pyridine
3-[4-(3-thienyl)-1,2,3,6-tetrahydropyridyl-methyl]-5-phenyl-pyridine
3-[1-(4-phenyl-1,2,3,6-tetrahydropyridyl)-ethyl]-5-phenyl-pyridine
3-[1-(4-phenyl-1,2,3,6-tetrahydropyridyl)-ethyl]-5-m-methoxyphenyl-pyridine
3-[1-(4-phenyl-1,2,3,6-tetrahydropyridyl)-ethyl]-5-p-methoxyphenyl-pyridine
3-[2-(4-phenyl-1,2,3,6-tetrahydropyridyl)-ethyl]-5-phenyl-pyridine
3-[2-(4-phenyl-1,2,3,6-tetrahydropyridyl)-ethyl]-5-m-methoxyphenyl-pyridine
3-[2-(4-phenyl-1,2,3,6-tetrahydropyridyl)-ethyl]-5-p-methoxyphenyl-pyridine
3-[3-(4-phenyl-1,2,3,6-tetrahydropyridyl)-propyl]-5-phenyl-pyridine, dihydrochloride, melting point: 239°–241°
3-[3-(4-phenyl-1,2,3,6-tetrahydropyridyl)-propyl]-5-m-methoxyphenyl-pyridine
3-[3-(4-phenyl-1,2,3,6-tetrahydropyridyl)-propyl]-5-p-methoxyphenyl-pyridine
3-(4-p-fluorophenyl-1,2,3,6-tetrahydropyridyl-methyl)-5-p-fluorophenyl-pyridine
3-[1-(4-p-fluorophenyl-1,2,3,6-tetrahydropyridyl)-ethyl]-5-p-fluorophenyl-pyridine
3-[2-(4-p-fluorophenyl-1,2,3,6-tetrahydropyridyl)-ethyl]-5-p-fluorophenyl-pyridine
3-[3-(4-p-fluorophenyl-1,2,3,6-tetrahydropyridyl)-propyl]-5p-fluorophenyl-pyridine
3-[2-(4-(2-thienyl)-1,2,3,6-tetrahydropyridyl)-ethyl]-5-phenyl-pyridine
3-[3-(4-(2-thienyl)-1,2,3,6-tetrahydropyridyl)-propyl]-5-phenyl-pyridine.

EXAMPLE 2

A mixture of 1.84 g of 3-aminomethyl-5-phenylpyridine (obtainable by reduction of 3-cyano-5-phenylpyridine with LiAlH$_4$) and 2.15 g of 1,5-dichloro-3-phenyl-2-pentene in 40 ml of acetone and 40 ml of water is boiled for 24 hours and worked up in the customary manner. "P", melting point: 80°–82°, is obtained.

EXAMPLE 3

A suspension of 4-phenyl-1-(5-phenylnicotinoyl)-1,2,3,6-tetrahydropyridine (melting point: 81°–83°; obtainable by reaction of 5-phenyl-nicotinic acid with 4-phenyl-1,2,3,6-tetrahydropyridine in the presence of carbonyldiimidazole in THF) in 200 ml of THF is added dropwise to a suspension of 3.8 g of LiAlH$_4$ in 200 ml of THF, with stirring. The mixture is stirred at 20° for a further 2 hours and worked up in the customary manner to give "P", melting point: 80°–82°.

The other compounds mentioned in Example 1 are obtained analogously from the corresponding acid amides.

EXAMPLE 4

3.62 g of 3-(4-hydroxy-4-phenyl-1-piperidyl-methyl)-5-p-fluorophenyl-pyridine (obtainable by reaction of 3-bromomethyl-5-p-fluorophenyl-pyridine with 4-piperidone, subsequent reaction with C$_6$H$_5$Li and hydrolysis) are heated at 50° with 40 ml of 1 N hydrochloric acid for 2 hours and the mixture is worked up in the customary manner to give 3-(4-phenyl-1,2,3, 6-tetrahydropyridyl-methyl)-5-p-fluorophenyl-pyridine, melting point: 128°–129°.

EXAMPLE 5

A mixture of 10 g of 3-(4-phenyl-1,2,3, 6-tetrahydropyridyl-methyl)-5-m-methoxyphenyl-pyridine and 10 g of pyridine hydrochloride is stirred at 160° for 3 hours. Customary working up gives 3-(4-phenyl-1,2,3, 6-tetrahydro-pyridyl-methyl)-5-m-hydroxyphenyl-pyridine. Dihydrochloride, melting point: 206°-208°.

EXAMPLE 6

A suspension of 3.56 g of 3-(4-phenyl-1,2,3, 6-tetrahydropyridyl-methyl)-5-m-methoxyphenyl)-pyridine in 50 ml of 1,2-dichloroethane is added dropwise to a boiling solution of 15.6 g of dimethyl sulfide-boron tribromide complex in 50 ml of 1,2-dichloroethane and the mixture is boiled for a further 30 minutes and worked up in the customary manner to give 3-(4-phenyl-1,2,3,6-tetrahydropyridyl-methyl)-5-m-hydroxyphenyl-pyridine, dihydrochloride, melting point: 206°-208°.

The following examples relate to pharmaceutical formulations containing amines of the formula I or their acid addition salts:

EXAMPLE A: TABLETS

A mixture of 1 kg of "P" dihydrochloride, 4 kg of lactose, 1.2 kg of potato starch, 0.2 kg of talc and 0.1 kg of magnesium stearate is pressed to tablets in the customary manner such that each tablet contains 10 mg of active compound.

EXAMPLE B: COATED TABLETS

Tablets are pressed analogously to Example A and are then coated in the customary manner with a coating consisting of sucrose, potato starch, talc, tragacanth and colorant.

EXAMPLE C: CAPSULES

Hard gelatine capsules are filled with 2 kg of "P" dihydrochloride in the customary manner so that each capsule contains 20 mg of the active compound.

EXAMPLE D: AMPOULES

A solution of 1 kg of "P" dihydrochloride in 60 l of doubly distilled water is subjected to sterile filtration, ampoules are filled with the solution, the solution is lyophilized under sterile conditions and the ampoules are sealed under sterile conditions. Each ampoule contains 10 mg of active compound.

Tablets, coated tablets, capsules and ampoules containing one or more of the remaining active compounds of the formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pyridine derivative of the formula

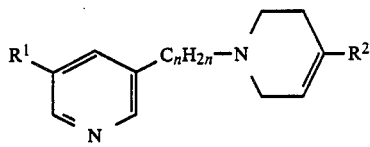

wherein each of $R^1$ and $R^2$ independently is phenyl, 2- or 3-thienyl, or phenyl monosubstituted or disubstituted by alkyl, alkoxy, F, Cl, Br, OH or $CF_3$, n is 1, 2 or 3, and alkyl and alkoxy each are of 1–4 C atoms or a physiologically acceptable acid addition salt thereof.

2. A compound of claim 1 wherein
$R^1$ is phenyl, tolyl, methoxyphenyl, fluorophenyl, chlorophenyl, hydroxyphenyl, trifluoromethylphenyl, dimethoxyphenyl.

3. A compound of claim 1 wherein
$R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl.

4. A compound of claim 1 wherein
$R^1$ is phenyl.

5. A compound of claim 1 wherein
$R^2$ is phenyl, tolyl, methoxyphenyl, fluorophenyl, chlorophenyl, trifluoromethylphenyl, chloro-trifluoromethylphenyl.

6. A compound of claim 1 wherein
$R^2$ is phenyl, o-, m- or p-tolyl, p-methoxyphenyl, p-fluorophenyl, p-chlorophenyl, m-trifluoromethylphenyl.

7. A compound of claim 1 wherein
$R^2$ is phenyl.

8. A compound of claim 1 wherein
$C_nH_{2n}$ is $-CH_2-$, $-CH(CH_3)-$, $-(CH_2)_2-$ or $-(CH_2)_3-$.

9. A compound of claim 1 wherein
$C_nH_{2n}$ is $-CH_2-$.

10. A compound of claim 1 wherein
$R^1$ is phenyl, o-, m- or p-tolyl, m- or p-methoxyphenyl, p-fluorophenyl, p-chlorophenyl, m- or p-hydroxyphenyl, m-trifluoromethylphenyl, 3,4-dimethoxyphenyl
$R^2$ is phenyl, o-, m- or p-tolyl, p-methoxyphenyl, p-fluorophenyl, p-chlorophenyl, m-trifluoromethylphenyl and
$C_nH_{2n}$ is $-CH_2-$, $-CH(CH_3)-$, $-(CH_2)_2-$ or $-(CH_2)_3-$.

11. A compound of claim 1 wherein
$R^1$ is phenyl, m- or p-methoxyphenyl, p-fluorophenyl, m-hydroxyphenyl or 3,4-dimethoxyphenyl,
$R^2$ is phenyl and
$C_nH_{2n}$ is $-CH_2-$.

12. 3-(4-Phenyl-1,2,3,6-tetrahydropyridyl-methyl)-5-phenyl-pyridine, a compound of claim 1.

13. A pharmaceutical composition for inducing a neuroleptic effect in a patient comprising an effective amount of a compound of claim 1 and a pharmaceutically acceptable carrier.

14. A composition of claim 13 wherein the amount of said compound is 0.2–500 mg.

15. A composition of claim 13 wherein the amount of said compound is 0.2–50 mg.

16. A method of causing a neuroleptic effect in a patient comprising administering to said patient an effective amount of a compound of claim 1.

17. A method of treating a patient suffering from psychosis comprising administering to said patient an effective amount of a compound of claim 1.

18. A method of treating a patient suffering from schizophrenia, psychoreactive disorders or psychopathies, or depressions comprising administering to said patient an effective amount of a compound of claim 1.

* * * * *